(12) United States Patent
Grass et al.

(10) Patent No.: US 9,280,837 B2
(45) Date of Patent: Mar. 8, 2016

(54) ANGIOGRAPHIC IMAGE ACQUISITION SYSTEM AND METHOD WITH AUTOMATIC SHUTTER ADAPTATION FOR YIELDING A REDUCED FIELD OF VIEW COVERING A SEGMENTED TARGET STRUCTURE OR LESION FOR DECREASING X-RADIATION DOSE IN MINIMALLY INVASIVE X-RAY-GUIDED INTERVENTIONS

(75) Inventors: Michael Grass, Buchholz in der Nordheide (DE); Dirk Schaefer, Hamburg (DE); Gert Antonius Franciscus Schoonenberg, Odiliapeel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1041 days.

(21) Appl. No.: 13/121,800

(22) PCT Filed: Oct. 7, 2009

(86) PCT No.: PCT/IB2009/054381
§ 371 (c)(1),
(2), (4) Date: Mar. 30, 2011

(87) PCT Pub. No.: WO2010/041201
PCT Pub. Date: Apr. 15, 2010

(65) Prior Publication Data
US 2011/0182492 A1 Jul. 28, 2011

(30) Foreign Application Priority Data

Oct. 10, 2008 (EP) .................................... 08166304

(51) Int. Cl.
*G06F 19/00* (2011.01)
*G06T 11/00* (2006.01)
(Continued)

(52) U.S. Cl.
CPC ................ *G06T 11/008* (2013.01); *A61B 6/06* (2013.01); *A61B 6/4441* (2013.01); *A61B 6/481* (2013.01);
(Continued)

(58) Field of Classification Search
CPC . G06F 19/321; G06F 19/3406; G06T 11/008; G06T 15/08; G06T 2211/404; A61B 6/06; A61B 6/4441; A61B 6/481; A61B 6/504; A61B 6/5247; A61B 6/542
See application file for complete search history.

(56) References Cited

U.S. PATENT DOCUMENTS

| 5,617,462 A | 4/1997 | Spratt |
| 6,055,295 A | 4/2000 | Murthy et al. |

(Continued)

FOREIGN PATENT DOCUMENTS

| DE | 3030332 A1 | 2/1982 |
| JP | 2005537843 A | 12/2005 |
| WO | 2005009243 A1 | 2/2005 |

OTHER PUBLICATIONS

Keall et al., "Geometric Accuracy of a Real-Time Target Tracking System With Dynamic Multileaf Collimator Tracking System", Int. J. Radiation Oncology Biol. Phys., vol. 65, No. 5, pp. 1579-1584, 2006.*

(Continued)

*Primary Examiner* — Katrina Fujita

(57) ABSTRACT

The present invention refers to an angiographic image acquisition system and method which can beneficially be used in the scope of minimally invasive image-guided interventions. In particular, the present invention relates to a system and method for graphically visualizing a pre-interventionally virtual 3D representation of a patient's coronary artery tree's vessel segments in a region of interest of a patient's cardiovascular system to be three-dimensionally reconstructed. Optionally, this 3D representation can then be fused with an intraoperatively acquired fluoroscopic 2D live image of an interventional tool. According to the present invention, said method comprises the steps of subjecting the image data set of the 3D representation associated with the precalculated optimal viewing angle to a 3D segmentation algorithm (S4) in order to find the contours of a target structure or lesion to be examined and interventionally treated within a region of interest and automatically adjusting (S5) a collimator wedge position and/or aperture of a shutter mechanism used for collimating an X-ray beam emitted by an X-ray source of a C-arm-based 3D rotational angiography device or rotational gantry-based CT imaging system to which the patient is exposed during an image-guided radiographic examination procedure based on data obtained as a result of said segmentation which indicate the contour and size of said target structure or lesion. The aim is to reduce the region of interest to a field of view that covers said target structure or lesion together with a user-definable portion of the surrounding vasculature.

18 Claims, 4 Drawing Sheets

(51) Int. Cl.
   *G06T 15/08* (2011.01)
   *A61B 6/00* (2006.01)
   *A61B 6/06* (2006.01)

(52) U.S. Cl.
   CPC .............. *A61B 6/504* (2013.01); *A61B 6/5247* (2013.01); *A61B 6/542* (2013.01); *G06F 19/321* (2013.01); *G06T 15/08* (2013.01); *G06F 19/3406* (2013.01); *G06T 2211/404* (2013.01)

(56) References Cited

U.S. PATENT DOCUMENTS

| | | | | |
|---|---|---|---|---|
| 6,775,399 | B1* | 8/2004 | Jiang | 382/128 |
| 7,340,033 | B2 | 3/2008 | Mollus et al. | |
| 8,155,405 | B2* | 4/2012 | Unal et al. | 382/128 |
| 8,457,439 | B2* | 6/2013 | Gu et al. | 382/275 |
| 2003/0086596 | A1* | 5/2003 | Hipp et al. | 382/128 |
| 2006/0153468 | A1* | 7/2006 | Solf | A61B 6/12 382/254 |
| 2006/0198799 | A1 | 9/2006 | Giniger | |
| 2007/0071172 | A1 | 3/2007 | Mollus et al. | |
| 2009/0082660 | A1* | 3/2009 | Rahn et al. | 600/411 |
| 2012/0328072 | A1 | 12/2012 | Shi et al. | |
| 2013/0343518 | A1 | 12/2013 | Noo et al. | |
| 2014/0146948 | A1 | 5/2014 | Zhang et al. | |
| 2014/0169525 | A1 | 6/2014 | Shimizu et al. | |
| 2014/0177782 | A1 | 6/2014 | Herold | |
| 2014/0275696 | A1 | 9/2014 | Dempsey et al. | |

OTHER PUBLICATIONS

Kitslaar et al., "Automated determination of optimal angiographic viewing angles for coronary artery bifurcations from CTA data", Feb. 2008, Proc. SPIE 6918, Medical Imaging 2008: Visualization, Image-guided Procedures, and Modeling, 69181J-1—69181J-10.*

BY G. Finet et al. "Optimizing Coronary Angiographic Views"; Department of Hemodynamics and Radiology, Hospices Civils de Lyon, Lyon, France, GE Medical Systems, Buc, France. international Journal of Cardiac Imaging 11 (Suppl1): pp. 53-54, 1995. Kluwer Academic Publishers. Printed in the Netherlands.

* cited by examiner

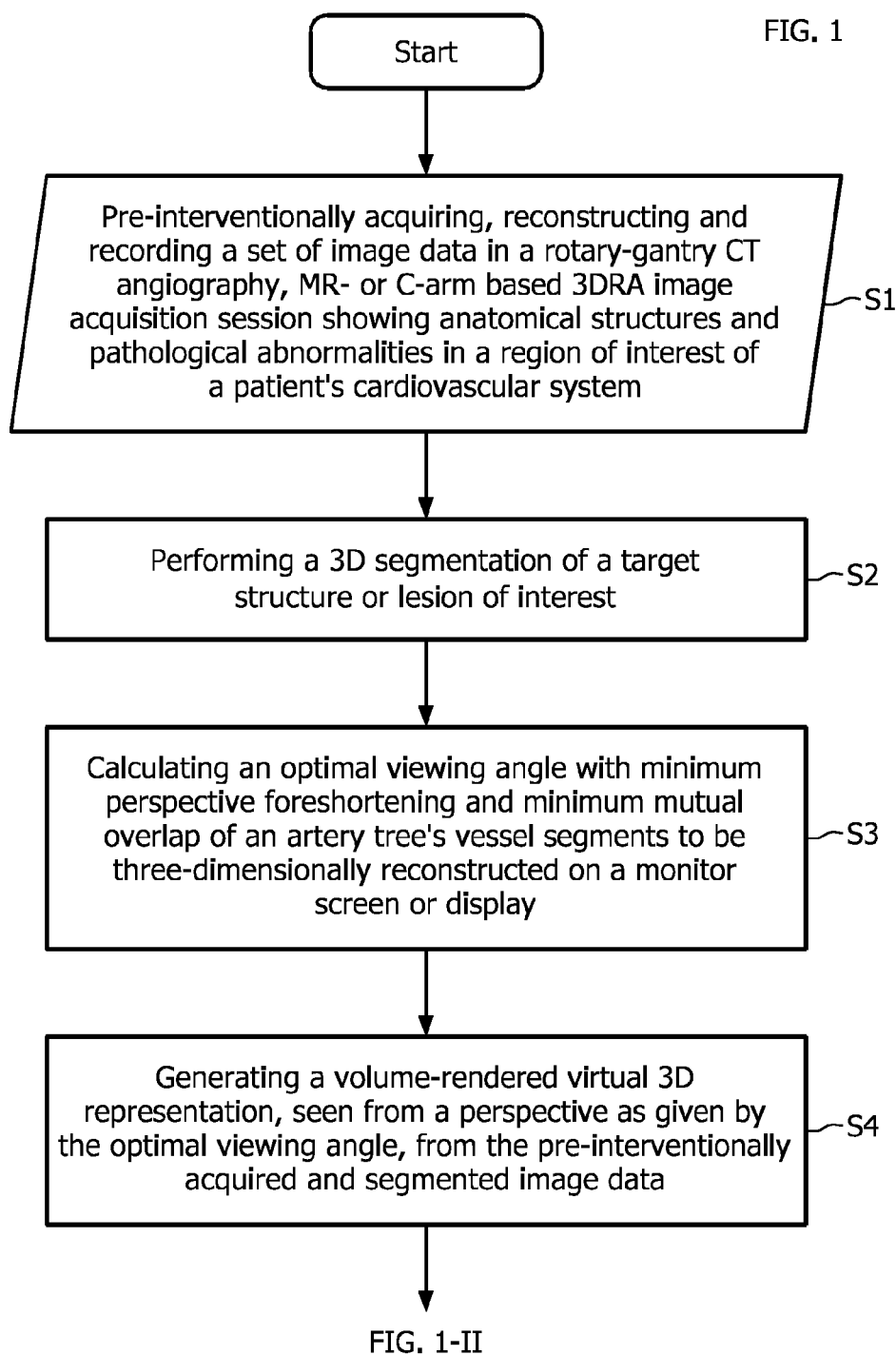

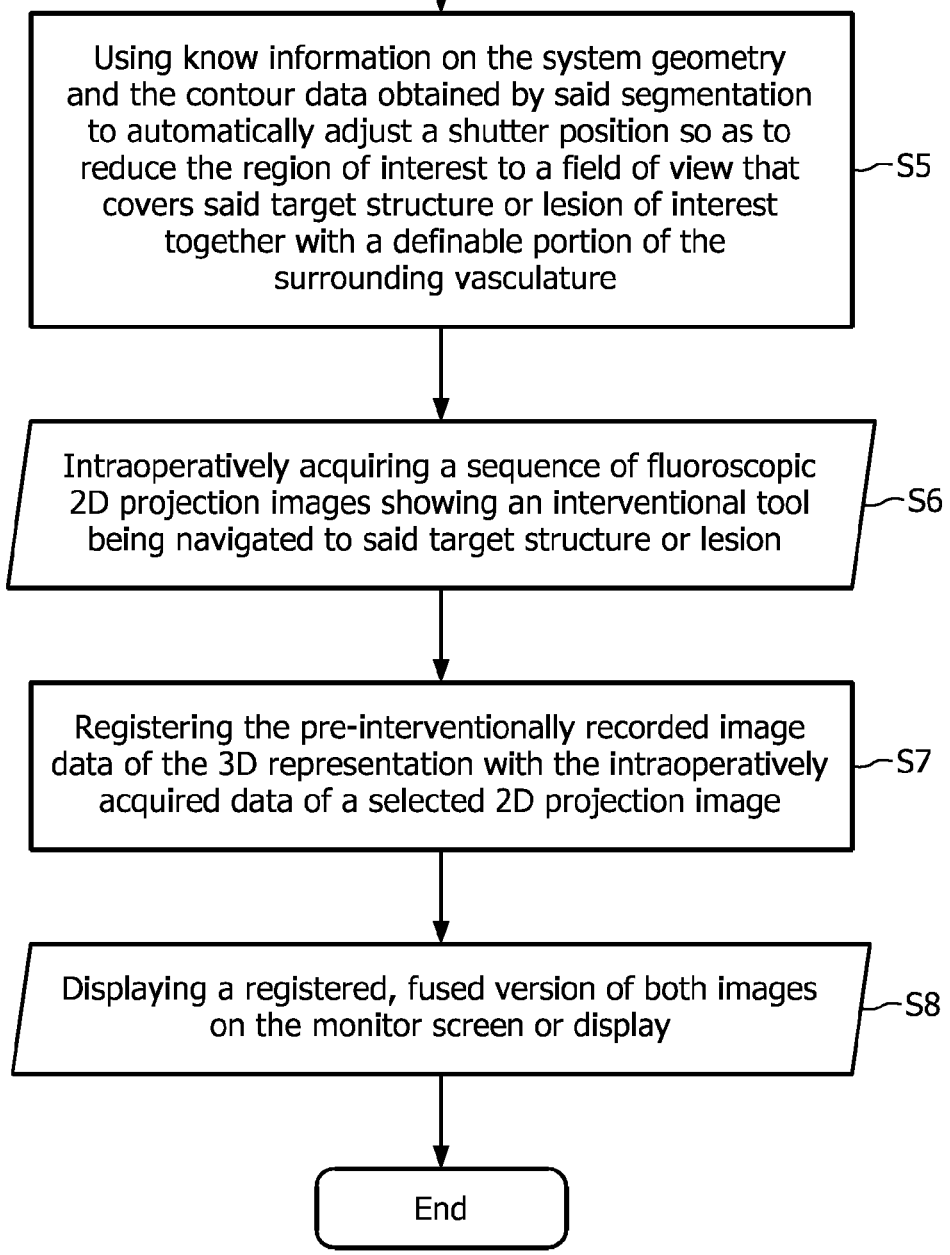
FIG. 1-II

ANGIOGRAPHIC IMAGE ACQUISITION SYSTEM AND METHOD WITH AUTOMATIC SHUTTER ADAPTATION FOR YIELDING A REDUCED FIELD OF VIEW COVERING A SEGMENTED TARGET STRUCTURE OR LESION FOR DECREASING X-RADIATION DOSE IN MINIMALLY INVASIVE X-RAY-GUIDED INTERVENTIONS

The present invention refers to an angiographic image acquisition system and method which can beneficially be used in the scope of minimally invasive image-guided interventions where image data showing an interventional tool while being navigated through a patient's cardiovascular and/or cardiac anatomy are intraoperatively acquired based on three-dimensional imaging and a set of image data for three-dimensionally reconstructing this anatomy are pre-interventionally acquired by means of MR, CT, C-arm-based 3DRA or any other imaging modality. In particular, the present invention relates to a system and method for graphically visualizing a pre-interventionally generated 3D representation of a patient's coronary artery tree's vessel segments in a region of interest of a patient's cardiovascular system to be three-dimensionally reconstructed, wherein said image acquisition is carried out by means of a conventional magnet resonance imaging system, a C-arm-based 3D rotational angiography apparatus, a computed tomography device of the rotary gantry type or any other type of 3D imaging modality. The pre-interventionally generated 3D representation thereby serves for cardiac interventional treatment planning and has an automatically reduced field of view which helps to decrease the required X-radiation dose to which a patient is exposed during the image-guided intervention procedure.

BACKGROUND OF THE INVENTION

Cardiovascular diseases (CVD), such as e.g. atherosclerosis, hypertension and ischemia, remain the leading cause of death in most developed countries as they cause permanent damage to the heart and blood vessels that may lead to chronic heart failure, angina, or myocardial infarction (heart attack). For a patient showing symptoms of a cardiovascular disease, primary diagnosis and treatment are usually performed via interventional cardiology in a cardiac catheterization laboratory. Cardiac catheterization thereby means insertion of small tubes (catheters) through arteries and/or veins to the myocard. In order to visualize coronary arteries and cardiac chambers with real-time X-ray imaging, a contrast agent is injected through the catheter. The contrast agent has to be opaque to X-rays and provide good image contrast as it flows into the coronary artery system or into the cardiac chambers. This procedure produces an image referred to as an angiogram, which is standard for diagnosing cardiovascular disease.

In the last thirty years, minimally invasive X-ray guided interventional cardiology has grown considerably, fueled by demographic, technologic and economic factors. New catheter-based interventional tools (such as e.g. balloon catheters and stents) allow physicians to treat more conditions and more complicated patient cases. As these new minimally invasive, image-guided procedures have positive patient outcomes and are less costly than open-heart procedures, physicians are actively encouraged by governmental and private payers to use these procedures for treating patients.

Nowadays, X-ray based cardiac catheterization systems represent the current standard of care and provide imaging modalities for both diagnostic and therapeutic procedures in cardiology. They are applied for generating real-time images of obstructions to blood flow in the coronary arteries. When an obstruction is identified, real-time X-ray imaging is utilized to guide insertion of balloon-tipped catheters to the point of obstruction for treatment by angioplasty (which means by balloon expansion of the restricted flow area in the artery) and stent placement (that is, by expanding a supporting structure to keep the newly enlarged artery open). The goal of therapy for patients with coronary artery disease is to alleviate symptoms of angina and reduce the risk of death or myocardial infarction by employing techniques and devices for re-opening the coronary arteries.

A cardiac catheterization system as mentioned above virtually enables all minimally invasive procedures in a catheterization laboratory. Currently developed systems all have the same fundamental architecture and use a point X-ray source that projects an X-ray beam through the patient and onto a large-area detector, the latter being used for converting the generated fluoroscopic image to electrical signals for display on a monitor. Thereby, a shadowgram image of the patient is obtained.

Conventionally employed cardiac catheterization systems typically perform two distinct types of real-time X-ray imaging: diagnostic angiography and interventional imaging. Diagnostic angiography is performed with a high radiation exposure in order to produce high-quality images. This diagnostic (cine) mode produces images of injected contrast agent flowing through the coronary arteries to diagnose the initial condition of the coronary arteries, determine the intervention required, and re-evaluate the coronary arteries after the intervention. Interventional imaging is performed with a regulated radiation exposure that produces lower-quality images. This interventional (fluoro) mode thereby provides real-time imaging of a patient's anatomy to guide the intervention and is used when inserting devices into the anatomy. The interventional mode is used for approximately 90% of the procedure imaging time.

Today, virtually all currently available conventional X-ray based cardiac catheterization systems, such as for example those developed and marketed by Philips Healthcare, Siemens Healthcare, GE Healthcare and Toshiba Medical Systems, use the same fundamental imaging technology, which has not changed dramatically over the past 40 years. Incremental improvements to individual components have optimized system performance over decades close to the theoretical limits. However, current systems still exhibit high radiation exposure. The key problems thereby relate to imaging, radiation hazards and operational issues.

One of the most difficult imaging tasks in the cardiac catheterization lab is imaging patients at steep viewing angles. With conventional systems, a large-area detector close to the patient causes more scattered radiation reaching the detector than image radiation, which thus may severely degrade the obtained image quality. Therefore, physicians often use a high-radiation diagnostic (cine) mode during interventions to obtain better quality images.

Another serious problem consists in the fact that overlying anatomy may inhibit viewing and navigation. Conventional cardiac catheterization systems produce a shadowgram image that shows objects with no depth information. Discerning 3-D anatomy from these flat images is difficult. In addition, image clutter and shadowing of the heart by ribs or the spine often degrades image clarity.

A further problem conventional X-ray based cardiac catheterization systems are typically faced with is exposing both the patient and the interventionalist to a significant amount of radiation. Prolonged exposure can cause radiation skin burns on patients and increase the risk of cancer to the interventionalists and catheterization lab staff. Preventative measures for physicians include use of heavy and cumbersome wrap-around lead aprons, vests and thyroid shields.

As briefly mentioned above, percutaneous transluminal coronary angiography procedures are associated with a significant amount of X-ray dose. The main task of such procedures is to place catheters or cardiovascular stents at a given location in the interior of the myocard or in a cardiac blood vessel, respectively. This is usually done under guidance of intraoperative X-ray imaging in order to visualize the position of the catheter tip. Intraoperative application of fluoroscopic X-ray imaging is often necessary to provide answers for a large number of questions. This is especially true, for instance, if an interventionalist needs to visualize the morphology of cardiac blood vessels. Apart from being applied in various interventional disciplines to assist in the placement of cardiac pacemakers, surgical stents and guide wires, this imaging modality is also used in orthopedic traumatology to enable the position monitoring of medical implants, orthopedic protheses as well as surgical screws and nails. In cardiac X-ray images, on the other hand, specific high-density anatomical structures (such as e.g. the spine, specific vertebras, etc.) or foreign objects (such as e.g. pacemaker leads and surgical stitches, etc.) are most of the time visible in the X-ray image and may thus at least partly obstruct or jeopardize the visibility, detection and/or tracking of interventional tools, either because they create similar patterns or because they cast a shadow on the objects which shall be detected. Classical image subtraction techniques do not help in case of slowly moving interventional tools and would require new acquisitions of reference sequences every time the 2D view changes.

For diagnosis and prognosis of coronary disease as well as for performance of catheter-based coronary interventions, a quantitative description of the coronary arterial tree including its 3D geometry is advantageous (currently, only 2D images are available to most of the cardiologists). From the prior art, many computer-assisted techniques for reconstructing three-dimensional views of the coronary artery tree from bi-plane projection images or multiple single-plane projection images acquired from different gantry positions of a C-arm system are known. However, due to the problem of vessel overlap and perspective foreshortening, multiple projections are necessary to adequately reconstruct the coronary arterial tree with arteriography. The elimination or at least reduction of perspective foreshortening and overlap is a necessary prerequisite for an accurate quantitative coronary analysis (QCA), such as determination of intercoronary lengths in a 2D display.

The relevant literature describes that in CT imaging optimal view maps (OVMs), which are generated in an effort to reduce perspective foreshortening, may be applied to aid a user in obtaining a gantry position of the imaging device which results in an optimal view. The article "Optimizing Coronary Angiographic Views" (Int. Journal Cardiac Imaging, Supplement 1, vol. 1, pp. 53-54, 1995) by G. Finet and J. Lienard, for example, focuses only on minimization of vessel perspective foreshortening relative to a single arterial segment. From the relevant state of the art it is known that prior to the process of reconstructing a virtual 3D representation in a specific region of interest of a patient's body volume, which may e.g. include the patient's coronary artery tree or cardiac chambers anatomy, it may be provided to calculate an optimal view map associated to the image data of said body volume. From this OVM, an optimal viewing direction with least perspective foreshortening and minimum vessel overlap for displaying a virtual 3D representation of said region of interest can then e.g. be derived by means of a color coding for distinguishing between optimal and less optimal viewing angles. Aside form calculating optimal view maps based on pre-interventionally acquired image data, it is also known from the state of the art to automatically guide a user or system to this viewing angle for projection acquisition during an intervention procedure. Sometimes, the 3D information is used as a roadmap to steer the C-arm manually in the desired position for viewing a lesion while reducing contrast agent and radiation dose to which the patient is exposed.

In the articles "A Viewpoint Determination System for Stenosis Diagnosis and Quantification in Coronary Angiographic Acquisition" (IEEE Trans. Med. Imag., vol. 17, no. 1, pp. 53-54, 1995) by Y. Sato, et al., and "3-D Coronary Angiography: Improving Visualization Strategy for Coronary Interventions" (in: Whats New In Cardiovascular Imaging, Kluwer Academic Publishers, pp. 61-67, 1998) by S. J. Chen and J. D. Carroll (hereinafter referred to as Chen and Carroll I), derivation of an optimal view strategy on the basis of minimization of both vessel overlap and perspective foreshortening is discussed. However, the technique devised by Sato requires a well-calibrated imaging system and manually specified correspondence in the 3D reconstruction process. Aside therefrom, the overlap measurement is limiting because it is performed based on the single stenotic segment with only immediate adjacent vessels. Sub-optimal solutions in determining optimal view are ineffective when the segment is more complex and more distal vessels were overlapped, both conditions of which are common in clinical conditions.

Conventional OVMs are typically utilized for an online reconstruction of a 3D arterial tree based on a pair of routine angiograms acquired from any two arbitrary viewing angles using single- or bi-plane imaging systems. A conventional process for reconstructing a virtual 3D representation of an object (such as e.g. a target structure or lesion) in a region of interest of a patient's cardiovascular system or cardiac anatomy which is optimized with respect to overlap and perspective foreshortening requires (a) an acquisition of two standard angiogram sequences by use of a single-plane imaging system, (b) an identification of 2D arterial trees and feature extractions, including bifurcation points, vessel diameters, vessel directional vertices, vessel centerlines, and construction of vessel hierarchies in the two images, (c) a determination of a transformation defining the spatial relationship of the acquired two views in terms of a rotation matrix and translation vector, and (d) a calculation of the 3D arterial (e.g., coronary) tree's arterial structures based thereon.

The approach discussed in the article "3-D Reconstruction of Coronary Arterial Tree to Optimize Angiographic Visualization" (IEEE Transactions on Medical Imaging, vol. 19, no. 4, April 2000) by S. J. Chen and J. D. Carroll (hereinafter referred to as Chen and Carroll II), on the other hand, requires considerable manual editing in order to retrieve the coronary tree. Chen and Carroll II thereby teaches the use two types of optimal view maps, a perspective foreshortening map and an overlap map, which two map types may be combined by the user to form a composite map, i.e. a "two-view" map.

Chen and Carroll II also teaches that an online 3D reconstruction technique, which is needed to reconstruct the entire coronary arterial trees based on two angiograms that have been acquired from two distinct projection directions without the need of a calibration object, and using a single-plane imaging system as well as a new optimization algorithm realized by minimizing the image point and vector angle errors in both views is subject to constraints which are derived from the intrinsic parameters of the single-plane imaging system.

Given the 3D character of the coronary artery tree, Chen and Carroll II expected that any projection would foreshorten a variety of segments. A reconstructed 3D coronary arterial tree may be rotated to any selected viewing angle yielding multiple computer-generated projections to determine for each patient which standard views are useful and which have no clinical value due to excessive overlap and perspective foreshortening. In this connection, Chen and Carroll II provide for computer-simulated projections for display with information of calculated percent perspective foreshortening and overlap on the screen such that a user may select any view by means of a keyboard input.

As an alternative to being reconstructed from pre-interventionally acquired CT or MR data sets which are to be registered with interventionally acquired fluoroscopic images, three-dimensional object representations can be obtained by means of straightforward 3D reconstruction or modeling of data sets from rotational C-arm based image acquisitions.

U.S. Pat. No. 7,340,033 B2 describes a method and a unit for automatically adjusting a collimator. In this connection, a region of interest inside the body is determined in an application-specific way from an analysis of first X-ray pictures, and the collimator is then adjusted thereon. The region of interest can, in particular, be chosen to be large enough for the irradiation field to cover all those positions of an organ of interest that occur as a result of heartbeat and/or respiration. Preferably, a data processing unit is designed to estimate the movement of the region of interest from an image analysis of subsequently acquired X-ray images during a current examination in order to be able to readjust the collimator if necessary. If the region of interest cannot be localized, the collimator is opened to a standard adjustment.

A method for automatically setting a collimator of an X-ray imaging system during image acquisition which includes receiving rapid scout images at an imaging station is disclosed in U.S. Pat. No. 6,055,295 A. The location of the body regions in one of said images is then automatically detected and used to generate settings for the collimator. The settings are used for automatically adjusting the collimator to substantially cover the non-body regions and substantially expose the body regions.

In U.S. Pat. No. 5,617,462 A, an automatic X-ray exposure control system and method for adjusting the X-ray dose/technique of X-ray diagnostic equipment to ensure sufficient doses/techniques for proper imaging while minimizing levels of radiation contacting the patient is described. A CCD video camera for analyzing the intensity of an acquired image is disposed adjacent to an X-ray receiver and opposite to an X-ray source. Said CCD video camera thereby provides two outputs, one of them being the absolute brightness as recorded by the camera. The obtained video signal is then analyzed by a windowing circuit or similar device to select an area of the image and restrict further processing of the image to that area. Circuits analyze the windowed area to detect the peak brightness and the average brightness within the windowed area. A microprocessor mathematically combines the readings to obtain a single value characteristic of the density of the piece of anatomy imaged by the X-ray equipment. The microprocessor then compares this value with one or more predetermined exposure control tables, determines the ideal dose/technique for imaging and adjusts the X-ray source to achieve ideal exposure. An automatic adjustment may then select predetermined techniques that may be used to minimize the X-ray radiation dose.

SUMMARY OF THE INVENTION

It may thus be an object of the present invention to describe an image acquisition device and method which helps to decrease the radiation dose required in the scope of minimally invasive image-guided interventions that are carried out based on a previously reconstructed virtual 3D representation of an anatomical object of interest (such as e.g. a vessel segment of a patient's cardiovascular system), a pathological target structure (e.g. a stenosis, an aneurysm, etc.) to be treated or any type of lesion to which an intervention device (such as e.g. a catheter brought into a patient's cardiovascular system) or implant (e.g. an angioplastic stent to be implanted during an intracoronary stent implantation procedure) has to be navigated.

To achieve this object, a first exemplary embodiment of the present invention is directed to an angiographic image acquisition method for acquiring and recording a set of image data used for three-dimensionally reconstructing a target structure or lesion in a region of interest of a patient's cardiovascular system to be graphically visualized, thereby yielding a virtual 3D representation of an artery tree's vessel segments located within said region of interest with said 3D representation being calculated and reconstructed such that said vessel segments are shown from the perspective of an optimal viewing angle yielding minimum perspective foreshortening and minimum vessel overlap. According to the present invention, said method comprises the steps of subjecting the image data set of the 3D representation associated with the precalculated optimal viewing angle to a 3D segmentation algorithm in order to find the contours of the target structure or lesion to be examined and interventionally treated within said region of interest and automatically adjusting a collimator wedge position and/or aperture of a shutter mechanism used for collimating an X-ray beam emitted by an X-ray source (such as e.g. an X-ray source of an interventional X-ray imaging system which can e.g. be C-arm based) to which said patient is exposed during an image-guided radiographic examination procedure based on data obtained as a result of said segmentation which indicate the contour and size of said target structure or lesion. The aim is to reduce the region of interest to a field of view that covers said target structure or lesion together with a user-definable portion of the surrounding vasculature.

In this connection, it may be provided that the automatic adjustment of the collimator wedge position and/or aperture of said shutter mechanism further depends on known geometrical setting parameters of the C-arm-based 3D rotational angiography device or rotational gantry-based CT imaging system used for acquiring the image data of the virtual 3D representation.

The size of the field of view obtained by automatically adjusting the collimator wedge position and/or aperture of said shutter mechanism may be readjustable to be manually readjusted by a user, and the portion of the surrounding vasculature to be displayed together with said target structure or lesion may be manually predefinable by the user by defining the thickness of a frame enclosing the segmented contours of said target structure or lesion.

In a preferred application scenario of this embodiment, the image data used for reconstructing said 3D representation are pre-interventionally acquired prior to a minimally invasive image-guided intervention procedure carried out on the patient's cardiovascular system for interventionally treating said target structure or lesion, and in this case said method additionally comprises the step of registering the virtual 3D representation with image data of the interventional X-ray imaging system, such as e.g. image data of a selected two-dimensional fluoroscopic live image, which is intraoperatively acquired during the minimally invasive image-guided intervention procedure. As a further option, the proposed angiographic image acquisition method as described above may comprise the step of displaying a registered, fused version of the 3D representation and the intraoperatively acquired image data, such as e.g. a two-dimensional fluoroscopic live image, on an angiography workstation's monitor screen or display. The image data for three-dimensionally reconstructing said region of interest may thereby be acquired by means of MR imaging, CT imaging, C-arm-based 3DRA imaging or any other type of imaging method and/or modality.

A second exemplary embodiment of the present invention is dedicated to an angiographic image acquisition method for determining, based on a sequence of virtual 3D representations for tracking a segmented target structure or lesion in a region of interest of a patient's cardiovascular system to be graphically visualized over the time, the optimal projection direction of this target structure or lesion with respect to overlap and perspective foreshortening for each of these 3D representations. It may thereby be provided that each 3D representation is generated by straightforward 3D reconstruction of an image data set that is being acquired in a 3DRA-based image acquisition session carried out during a minimally invasive image-guided intervention procedure for interventionally treating said target structure or lesion. According to this embodiment, said method thereby comprises the step of automatically adjusting a collimator wedge position and/or aperture of a shutter mechanism used for collimating an X-ray beam emitted by an X-ray source to which said patient is exposed during an image-guided radiographic examination procedure based on data obtained as a result of a dynamically updated segmentation which indicate the contour and size of the target structure or lesion so as to reduce the region of interest to a field of view that covers said target structure or lesion together with a user-definable portion of the surrounding vasculature, wherein said field of view is continually resized dependent on the dynamically updated segmentation.

A third exemplary embodiment of the present invention relates to a collimator control unit of an angiographic image acquisition device for acquiring and recording a set of image data used for three-dimensionally reconstructing a target structure or lesion in a region of interest of a patient's cardiovascular system to be graphically visualized with said reconstruction yielding a virtual 3D representation of an artery tree's vessel segments located within said region of interest and with said 3D representation being calculated and reconstructed such that said vessel segments are shown from an optimal viewing angle with minimum perspective foreshortening and minimum vessel overlap. According to the present invention, said angiographic image acquisition device is programmed for subjecting the image data set of the 3D representation associated with the precalculated optimal viewing angle to a 3D segmentation algorithm to find the contours of the target structure or lesion to be examined and interventionally treated within said region of interest. The collimator control unit, on the other hand, is adapted for automatically adjusting a collimator wedge position and/or aperture of a shutter mechanism used for collimating an X-ray beam emitted by an X-ray source (such as e.g. an interventional X-ray imaging system which can e.g. be C-arm based) to which said patient is exposed during an image-guided radiographic examination procedure based on data obtained as a result of said segmentation which indicate the contour and size of said target structure or lesion. The aim is to reduce the region of interest to a field of view that covers said target structure or lesion together with a user-definable portion of the surrounding vasculature.

In this connection, it may be provided that the collimator control unit is adapted for automatically adjusting the collimator wedge position and/or aperture of said shutter mechanism additionally based on known geometrical setting parameters of the C-arm-based 3D rotational angiography device or rotational gantry-based CT imaging system which is used for acquiring the image data of the virtual 3D representation.

Furthermore, said collimator control unit may be adapted for manually readjusting the size of the field of view obtained by automatically adjusting the collimator wedge position and/or aperture of said shutter mechanism, and it may further be adapted for manually predefining the portion of the surrounding vasculature to be displayed together with said target structure or lesion by defining the thickness of a frame enclosing the segmented contours of said target structure or lesion.

Aside therefrom, a fourth exemplary embodiment of the present invention is dedicated to an angiographic image acquisition device for acquiring and recording a set of image data used for three-dimensionally reconstructing a target structure or lesion in a region of interest of a patient's cardiovascular system to be graphically visualized a with said reconstruction yielding a virtual 3D representation of an artery tree's vessel segments located within said region of interest and with said 3D representation being calculated and reconstructed such that said vessel segments are shown from an optimal viewing angle with minimum perspective foreshortening and minimum vessel overlap. According to the present invention, said angiographic image acquisition device thereby comprises a collimator control unit as described above with reference to said second exemplary embodiment.

In a preferred application scenario of this embodiment, said image data used for generating said 3D representation may be pre-interventionally acquired prior to a minimally invasive image-guided intervention procedure carried out on the patient's cardiovascular system for interventionally treating said target structure or lesion, and in this case said angiographic image acquisition device may be additionally adapted for registering the virtual 3D representation with image data of a selected two-dimensional fluoroscopic live image intraoperatively acquired during the minimally invasive image-guided intervention procedure.

As a further option, the proposed angiographic image acquisition device as described above may additionally be adapted for displaying a registered, fused version of the virtual 3D representation and the intraoperatively acquired two-dimensional fluoroscopic live image on an angiography workstation's monitor screen or display.

Finally, according to a fifth exemplary embodiment of the present invention, a computer software product configured for performing a method as described above with reference to said first exemplary embodiment when running on a data processing means of an angiographic image acquisition device as described above with reference to said fourth exemplary embodiment is provided.

BRIEF DESCRIPTION OF THE DRAWINGS

These and other advantageous aspects of the invention will be elucidated by way of example with respect to the embodiments described hereinafter and with respect to the accompanying drawings. Therein, FIG. 1 shows a flowchart which illustrates the proposed image acquisition method according to said first exemplary embodiment of the present invention.

DETAILED DESCRIPTION OF THE PRESENT INVENTION

Figure 2A:
FIG. 2a shows a perspective volume rendering of a set of pre-interventionally acquired image data of a patient's left coronary artery tree seen from an optimal viewing angle yielding minimum perspective foreshortening and minimum vessel overlap.

In the following, the proposed image acquisition device and method according to the present invention will be explained in more detail with respect to special refinements and referring to the accompanying drawings.

The flowchart depicted in FIG. 1 illustrates the proposed image acquisition method according to the above-described first exemplary embodiment of the present invention. The proposed method begins with the step of pre-interventionally acquiring, reconstructing and recording (S1) a set of image data in a rotary-gantry based CT angiography imaging, MR- or C-arm based 3DRA image acquisition session, said image data showing anatomical structures and/or pathological abnormalities in a region of interest of a patient's cardiovascular system to be examined and treated by executing a minimally invasive image-guided intervention. These image data are then subjected to a 3D segmentation algorithm (S2) in order to find the contours and, optionally, calculate the size of a target structure or lesion of interest. Further optionally, this step may be followed by a contrast enhancement process which is applied to the segmented image (not shown). Next, an optimal viewing angle with minimum perspective foreshortening and minimum vessel overlap of an artery tree's vessel segments to be displayed is calculated (S3) such that a virtual 3D representation to be reconstructed can be displayed on an angiography workstation's monitor screen or display. After this preoperative image acquisition step, a volume-rendered 3D representation, seen from a perspective as given by the optimal viewing angle, is generated (S4) from the pre-interventionally acquired and segmented image data. Based on known geometrical parameter settings of the respectively applied image acquisition device and based on the contour data (and/or size data) obtained by the 3D segmentation algorithm mentioned above, the collimator wedge position and/or aperture of a shutter mechanism used for collimating an X-ray beam emitted by an X-ray source of a C-arm-based 3D rotational angiography device or rotational gantry-based CT imaging system to which said patient is exposed during an image-guided radiographic examination procedure (such as e.g. a collimator mounted to an X-ray source of a CT angiography system which is used for image acquisition) is automatically adjusted (S5) so as to reduce the region of interest to a field of view that covers said target structure or lesion of interest together with a user-definable portion of the surrounding vasculature. The pre-interventionally acquired and recorded image data of the segmented target structure or lesion located in the automatically collimated field of view may then e.g. be registered (S7) with a selected image from an intraoperatively acquired (S6) sequence of fluoroscopic 2D projection images showing an interventional tool being navigated to said target structure or lesion. The registering procedure thereby yields a best match between the virtual 3D representation and the selected fluoroscopic image. Finally, a registered, fused version of both images may be displayed (S8) on the monitor screen or display.

Instead of performing steps S6 to S8, it could optionally be provided to display said 3D representation from the perspective of a viewing angle which is optimal with respect to overlap and perspective foreshortening together with virtual shutters needed for fading out a frame range outside an automatically selected field of view, wherein the thickness of said frame range is to be interactively accepted or refused by a user. On the condition that the thickness of said frame range has been accepted by the user, an image-guided interventional procedure can be carried out.

In FIG. 2a, a perspective volume rendering of a set of pre-interventionally acquired image data showing a patient's left coronary artery tree seen from a perspective as given by the optimal viewing angle which has been determined from the parameter space of an optimal view map with said viewing angle yielding minimum perspective foreshortening and minimum vessel overlap is depicted. Instead of applying a volume rendering technique, the three-dimensional impression can also be obtained by employing a multiplanar reformation procedure or surface-shaded display algorithm to the set of previously acquired image data.

Figure 2B:
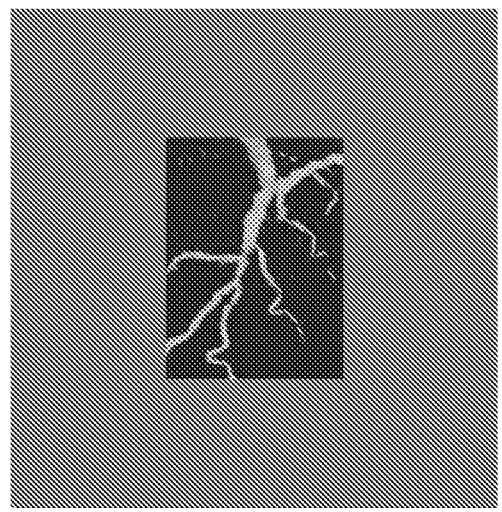
FIG. 2b shows a reduced field of view of the perspective volume rendering sketched in FIG. 2a with non-interesting parts of said image being faded out by a colored frame.

A selected field of view of the perspective volume rendering sketched in FIG. 2a with non-interesting parts of said image being faded out by a colored frame is shown in FIG. 2b. The length, width and center position of the depicted field of view thereby depend on the collimator wedge position and/or aperture of a shutter mechanism used for collimating an X-ray beam emitted by an X-ray source of a C-arm-based 3D rotational angiography device or rotational gantry-based CT imaging system to which said patient is exposed during an image-guided radiographic examination procedure carried out for acquiring said image. To be more precise, said length, width and center position are determined based on the contour and size of an identified target structure or lesion and, optionally, based on known geometrical setting parameters of the applied image acquisition device.

Figure 3:
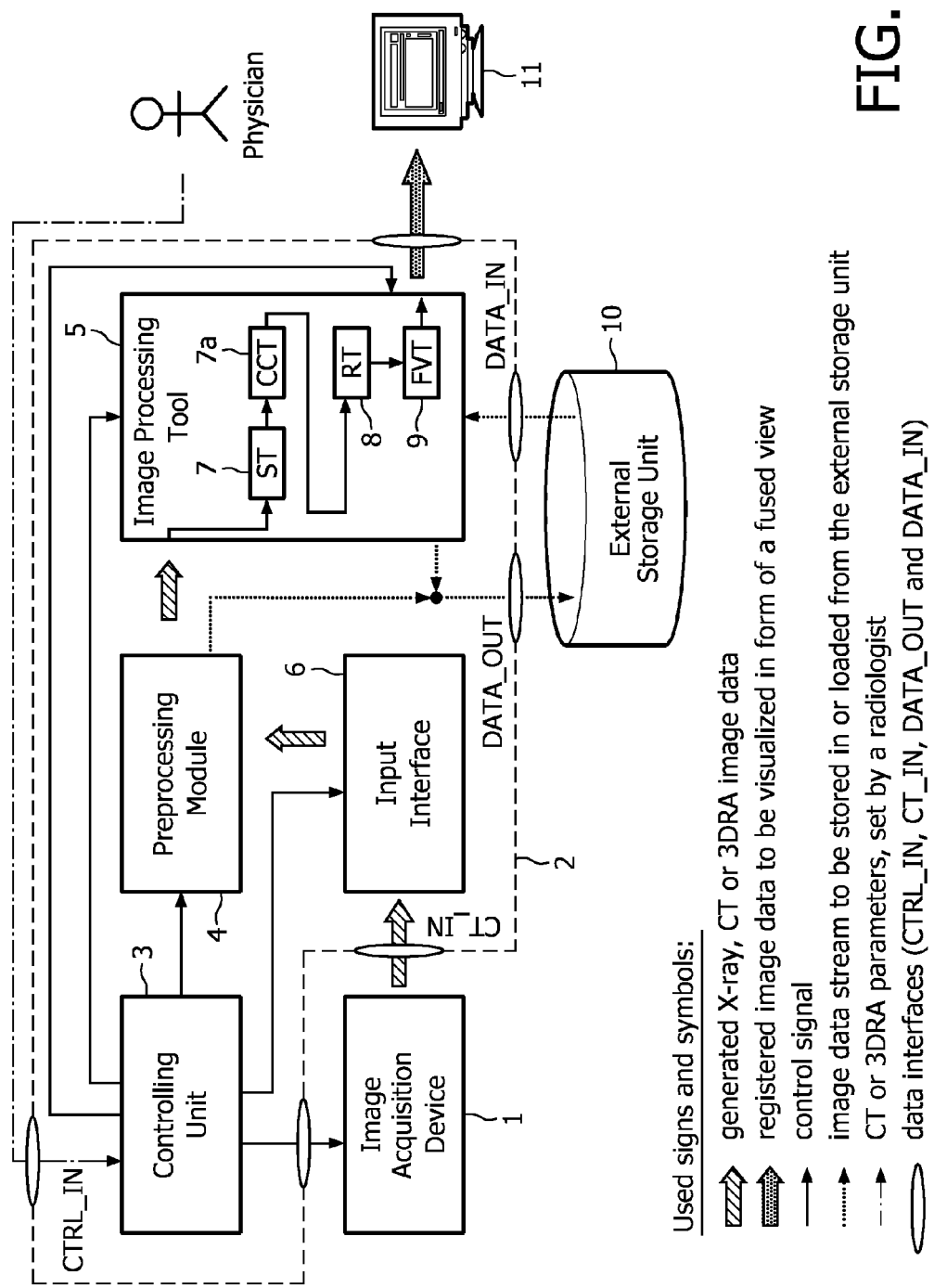
FIG. 3 shows a schematic block diagram of an imaging system according to said fourth exemplary embodiment of the present invention.

FIG. 3 shows a schematic block diagram of an imaging system 2 according to an exemplary embodiment of the present invention which makes it possible to store, process and visualize acquired image data showing an anatomical structure or a specific region of interest, pathological abnormalities, interventional tools, pacemakers, angioplastic stents or other implants in a blood vessel segment of a patient's vascular system on a monitor screen of an angiography workstation 11 connected to said imaging system 2. The image data may e.g. be given in the form of intraoperatively acquired 2D fluoroscopic images, volume-rendered image data or pre-interventionally recorded image data which are generated and provided by an image acquisition device 1, such as e.g. by a conventional X-ray system, a rotary-gantry computed tomography (CT) system or a C-arm based 3D rotational angiography (3DRA) device. The acquired 2D and reconstructed 3D image data can either be visualized in different windows or in a common window showing a fused view of a digitally reconstructed radiograph that has been generated from the pre-interventionally recorded image data and an intraoperatively acquired 2D fluoroscopic image which has been co-registered with said digitally reconstructed radiograph.

As shown in FIG. 3, image data generated by said image acquisition device 1 are fed to the imaging system 2 via an input interface 6. Aside from a controlling unit 3 which controls the data exchange with the image acquisition device 1, said imaging system 2 may comprise a preprocessing module 4 which may particularly be equipped with a digital filter for noise reduction and contrast enhancement. An image processing tool 5, integrated in said imaging system, may serve for generating volume-rendered 3D views, surface-shaded display (SSD) images, multiplanar reformatted images and/or digitally reconstructed radiographs that are rendered based on the generated image data of an anatomical structure or pathological abnormality in a region of interest of a patient's cardiovascular system to be examined and interventionally treated.

As exemplarily depicted in the block diagram shown in FIG. 3, said image processing tool 5 may be equipped with a segmentation tool 7 for determining the contours of a target structure or lesion located within said region of interest as well as with a registration tool 8 for determining the parameters of a 2D/3D registration mapping used for registering the pre-interventionally reconstructed 3D representation with an intraoperatively acquired 2D fluoroscopic image. The above-mentioned collimator control unit is referred to by reference number 7a. A fusing and visualization tool 9, which may also be integrated in said image processing tool 5, may serve for generating and displaying a fused image of the virtual 3D representation and the 2D fluoroscopic image after being submitted to said 2D/3D registration.

As shown in FIG. 3, image data that have been generated by the image acquisition device 1 and supplied to the imaging system 2 via said input interface 6 may temporarily or persistently be stored in an image data archive of an external storage unit 10 via data output interface DATA_OUT. For being visualized, the stored image data can be loaded via a data input interface, in FIG. 3 referred to as "DATA_IN", into a local temporary storage of imaging system 2 (not shown), thereby using a standardized data format (such as e.g. the DICOM format).

Applications of the Present Invention

The present invention can advantageously be applied in the scope of minimally invasive image-guided interventions where it is beneficial to reduce the field of view to be displayed on a monitor screen or display in order to reduce an X-radiation dose to which a patient to be examined and treated is exposed during a radiographic image acquisition session. In particular, the invention can be beneficially applied in a medical workstation or console of an interventional X-ray imaging system.

While the present invention has been illustrated and described in detail in the drawings and in the foregoing description, such illustration and description are to be considered illustrative or exemplary and not restrictive, which means that the invention is not limited to the disclosed embodiments. Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures can not be used to advantage. A computer program may be stored/distributed on a suitable medium, such as e.g. an optical storage medium or a solid-state medium supplied together with or as part of other hardware, but may also be distributed in other forms, such as e.g. via the Internet or other wired or wireless telecommunication systems. Furthermore, any reference signs in the claims should not be construed as limiting the scope of the present invention.

The invention claimed is:

1. An angiographic image acquisition method for determining, based on a virtual three-dimensional (3D) representation of a region of interest in a patient's cardiovascular system to be graphically visualized, the optimal projection direction of a segmented target structure, or segmented target lesion, with respect to overlap and perspective foreshortening, said method comprising the step of automatically adjusting a collimator wedge position and/or aperture of a shutter mechanism used for collimating an X-ray beam emitted by an X-ray source to which said patient is exposed during an image-guided radiographic examination procedure based on data obtained as a result of the segmentation which indicate the contour and size of said target structure or lesion so as to reduce the region of interest to a field of view that covers said target structure or lesion together with a user-definable portion of the surrounding vasculature, said method being based on a method of virtual 3D representations for tracking a target structure or lesion over time, said method being applied to each of said virtual 3D representations and the segmentation is updated dynamically.

2. The angiographic image acquisition method according to claim 1, said method comprising, prior to said determining, the step of subjecting an acquired image data set needed for reconstructing said 3D representation to a 3D segmentation algorithm in order to find the contours of said target structure or lesion within said region of interest.

3. The angiographic image acquisition method according to claim 2, wherein the automatic adjustment of the collimator wedge position and/or aperture of said shutter mechanism further depends on known geometrical setting parameters of a C-arm-based 3D rotational angiography device or a rotational gantry-based CT imaging system used for acquiring the image data of the virtual 3D representation.

4. The angiographic image acquisition method according to claim 1, wherein the size of the field of view obtained by automatically adjusting the collimator wedge position and/or aperture of said shutter mechanism is readjustable to be manually readjusted by a user.

5. The angiographic image acquisition method according to claim 4, wherein the portion of the surrounding vasculature to be displayed together with said target structure or lesion can be manually predefined by the user by defining the thickness of a frame enclosing the segmented contours of said target structure or lesion.

6. The angiographic image acquisition method according to claim 4, wherein the image data used for generating said 3D representation are pre-interventionally acquired prior to a minimally invasive image-guided intervention procedure carried out on the patient's cardiovascular system for interventionally treating said target structure or lesion, said method additionally comprising the step of registering the virtual 3D representation with image data of a selected two-dimensional fluoroscopic live image intraoperatively acquired during the minimally invasive image-guided intervention procedure.

7. The angiographic image acquisition method according to claim 6, additionally comprising the step of displaying a registered, fused version of the virtual 3D representation and the intraoperatively acquired two-dimensional fluoroscopic live image on an angiography workstation's monitor screen or display.

8. An angiographic image acquisition method according to claim 7, wherein the image data for three-dimensionally reconstructing said region of interest are pre-interventionally acquired by means of MR imaging, CT imaging, C-arm-based 3DRA imaging or any other type of imaging method and/or modality.

9. An angiographic image acquisition method for determining, based on a sequence of virtual three-dimensional (3D) representations for tracking a segmented target structure, or segmented target lesion, in a region of interest of a patient's cardiovascular system to be graphically visualized over the time, the optimal projection direction of this target structure or lesion with respect to overlap and perspective foreshortening for each of these 3D representations, wherein each 3D representation is generated by straightforward 3D reconstruction of image data sets that are being acquired in a 3DRA-based image acquisition session carried out during a minimally invasive image-guided intervention procedure for interventionally treating said target structure or lesion, said method comprising the step of automatically adjusting a collimator wedge position and/or aperture of a shutter mechanism used for collimating an X-ray beam emitted by an X-ray source to which said patient is exposed during an image-guided radiographic examination procedure based on data obtained as a result of a dynamically updated segmentation which indicate the contour and size of the target structure or lesion so as to reduce the region of interest to a field of view that covers said target structure or lesion together with a user-definable portion of the surrounding vasculature, wherein said field of view is continually resized dependent on the dynamically updated segmentation.

10. The method of claim 9, said tracking serving to track over time.

11. A medical image acquisition device for acquiring and recording a set of image data used for three-dimensionally reconstructing a target structure or lesion in a region of interest of a patient's cardiovascular system to be graphically visualized, thereby yielding a virtual 3D representation of an artery tree's vessel segments located within said region of interest with said 3D representation being calculated and reconstructed such that said vessel segments are shown from an optimal viewing angle with minimum perspective foreshortening and minimum vessel overlap, wherein said image acquisition device is configured for determining, based on a virtual three-dimensional representation of a region of interest in a patient's cardiovascular system to be graphically visualized, the optimal projection direction of a segmented target structure or lesion with respect to overlap and perspective foreshortening, said device comprising a collimator control unit configured for automatically adjusting a collimator wedge position and/or aperture of a shutter mechanism used for collimating an X-ray beam emitted by an X-ray source to which said patient is exposed during an image-guided radiographic examination procedure based on data obtained as a result of the segmentation which indicate the contour and size of said target structure or lesion so as to reduce the region of interest to a field of view that covers said target structure or lesion together with a user-definable portion of the surrounding vasculature, said image acquisition device being further configured for manually predefining the portion of the surrounding vasculature to be displayed together with said target structure or lesion by defining the thickness of a frame enclosing said contour.

12. The image acquisition device according to claim 11, configured for automatically adjusting the collimator wedge position and/or aperture of said shutter mechanism additionally based on known geometrical setting parameters of the C-arm-based 3D rotational angiography device or rotational gantry-based CT imaging system which is used for acquiring the image data of the virtual 3D representation.

13. The image acquisition device according to claim 11, configured for manually readjusting the size of the field of view obtained by automatically adjusting the collimator wedge position and/or aperture of said shutter mechanism.

14. The medical image acquisition device according to claim 11 with said image data used for generating said 3D representation being pre-interventionally acquired prior to a minimally invasive image-guided intervention procedure carried out on the patient's cardiovascular system for interventionally treating said target structure or lesion, said medical image acquisition device being additionally configured for registering the virtual 3D representation with image data of a selected two-dimensional fluoroscopic live image intraoperatively acquired during the minimally invasive image-guided intervention procedure.

15. The medical image acquisition device according to claim 14, additionally configured for displaying a registered, fused version of the virtual 3D representation and the intraoperatively acquired two-dimensional fluoroscopic live image on an angiography workstation's monitor screen or display.

16. A non-transitory computer readable medium embodying a program for X-ray exposure reduction, said program having instructions executable by a processor for performing a plurality of acts, among said plurality there being the acts of:
  determining, based on a virtual three-dimensional (3D) representation of a region of interest in a patient's cardiovascular system, the optimal projection direction of a segmented target structure, or segmented target lesion, with respect to overlap and perspective foreshortening;
  automatically adjusting a collimator wedge position and/or aperture of a shutter mechanism used for collimating an X-ray beam emitted by an X-ray source to which said patient is exposed during an image-guided radiographic examination procedure based on data obtained as a result of the segmentation which indicate the contour and size of said target structure or lesion so as to reduce the region of interest to a field of view that covers said target structure or lesion together with a user-definable portion of the surrounding vasculature;
  displaying said 3D representation;
  automatically selecting, as a display field of view enclosing said contour, a field of view for said displaying;
  displaying virtual shutters that define a thickness of a frame enclosing said display field of view;
  receiving an interactive user-instruction that either accepts or refuses said thickness; and
  recognizing, based on the received user-instruction, an acceptance of said thickness.

17. The computer readable medium of claim 16, said displaying of said 3D representation being from the perspective of said optimal projection direction.

18. A medical image acquisition device comprising an X-ray collimating processor and collimator control circuitry, said processor being configured for determining, based on a virtual three-dimensional (3D) representation of a region of interest in a patient's cardiovascular system to be graphically visualized, the optimal projection direction of a segmented target structure, or segmented target lesion, with respect to overlap and perspective foreshortening, said circuitry being configured for automatically adjusting a collimator wedge position and/or aperture of a shutter mechanism used for collimating an X-ray beam emitted by an X-ray source to which said patient is exposed during an image-guided radiographic examination procedure based on data obtained as a result of the segmentation which indicate the contour and size of said target structure or lesion so as to reduce the region of interest to a field of view that covers said target structure or lesion together with a user-definable portion of the surrounding vasculature, said processor being further configured for using a plurality of virtual 3D representations for tracking a target structure or lesion over time, and for performing said determining, and said adjusting, for each of said virtual 3D representations, said segmentation being updated dynamically.

* * * * *